US 8,545,826 B2

(12) United States Patent
Bräutigam et al.

(10) Patent No.: US 8,545,826 B2
(45) Date of Patent: Oct. 1, 2013

(54) COSMETIC COMPOSITION

(75) Inventors: Ina Bräutigam, Darmstadt (DE); Frank Hermes, Seeheim (DE)

(73) Assignee: KAO Germany GmbH, Darmstadt (DE)

( * ) Notice: Subject to any disclaimer, the term of this patent is extended or adjusted under 35 U.S.C. 154(b) by 97 days.

(21) Appl. No.: 12/874,355

(22) Filed: Sep. 2, 2010

(65) Prior Publication Data

US 2010/0319719 A1  Dec. 23, 2010

Related U.S. Application Data

(62) Division of application No. 11/423,730, filed on Jun. 13, 2006, now abandoned.

(30) Foreign Application Priority Data

Jun. 14, 2005 (EP) .................. 05012717

(51) Int. Cl.
*A61K 8/02* (2006.01)
(52) U.S. Cl.
USPC ..................... 424/70.11
(58) Field of Classification Search
None
See application file for complete search history.

(56) References Cited

U.S. PATENT DOCUMENTS

| | | | |
|---|---|---|---|
| 5,620,684 A | | 4/1997 | Dupuis |
| 5,839,623 A * | | 11/1998 | Losenno et al. ........... 222/402.1 |
| 6,468,549 B1 | | 10/2002 | Dupuis et al. |
| 6,905,674 B2 * | | 6/2005 | L'Alloret .................... 424/59 |
| 7,053,146 B2 * | | 5/2006 | Morschhauser et al. ...... 524/461 |
| 7,108,860 B2 | | 9/2006 | Dueva et al. |
| 2005/0053561 A1 | | 3/2005 | Suginaka |
| 2005/0249684 A1 | | 11/2005 | Dobkowski et al. |
| 2006/0084586 A1 * | | 4/2006 | Drzewinski et al. ......... 510/119 |

FOREIGN PATENT DOCUMENTS

| | | |
|---|---|---|
| EP | 0 521 666 A1 | 7/1993 |
| WO | 2004/063228 A1 | 7/2004 |

* cited by examiner

*Primary Examiner* — Anand Desai
*Assistant Examiner* — Melissa Mercier
(74) *Attorney, Agent, or Firm* — Norris McLaughlin & Marcus, P.A.

(57) ABSTRACT

Present invention is on styling composition comprising at least one film forming polymer, at least one polyol at a concentration of 5% by weight or higher and polyacryloldimethyltaurate and/or its salts. The composition of the present invention improves curl retention, curl separation, shine and manageability of hair.

19 Claims, No Drawings

COSMETIC COMPOSITION

This is a divisional patent application of U.S. Ser. No. 11/423,730, which was filed on Jun. 13, 2006.

The present invention is related to a hair styling compositions with improved curl retention, curl separation, shine and manageability effects.

Styling compositions have been known for decades. They are used after usual hair conditioning cycle to give hair better and long lasting hold, to improve hair volume or simply to fix the hair so that the hair does not move naturally.

Although the extensive studies available in the prior art, improvements are still needed especially in obtaining long lasting curly appearance, better shine and easy to manageable hair.

The inventors of the present invention has found out surprisingly that a hair styling composition based on a film forming polymer and comprising furthermore at least 5% by weight of the total composition a polyol and an anionic polymer, polyacryloyl dimethyl taurate and/or its salts improves the curl retention and curl separation, gives hair excellent shine and hair is easily stylable—improved manageability.

The term curl separation means that curls appears in a tidy way with waves. In a hair streak with no curl separation curls can not be clearly identified.

Further object of the present invention is the use of a composition comprising at least one film forming polymer, at least 5% by weight of the total composition a polyol and an anionic polymer, polyacryloyl dimethyl taurate and/or its salts for improving curl retention, curl separation, shine and manageability of hair Still further object of the present invention is a process for improving shine, manageability and curl retention of curly hair characterised in that on a shampooed and towel dried hair a composition comprising at least one film forming polymer, at least 5% by weight of the total composition a polyol and an anionic polymer, polyacryloyl dimethyl taurate and/or its salts is applied and the hair is air-dried or dried with electrical hair drier.

WO 2004/063228 A1 discloses compositions with the anionic polymer polyacryloyl dimethyl taurate and its sodium salts. The compositions disclosed therein are mainly in the skin care compositions and no styling compositions have been included.

The compositions of the present invention comprise at least one film forming polymer. The polymer is selected from the anionic, non-ionic, cationic and/or amphoteric or zwitterionic ones. The most preferred ones are the non-ionic and anionic types. The presence of the other types is possible in combination with the non-ionic ones.

Non-ionic polymers are selected from the ones soluble in water and/or alcohol and/or in alcohol water mixtures, at any ratio. Under the definition of soluble in alcohol and alcohol water mixture, it should be understood that the polymer is soluble in lower alcohols such as ethanol, n-propanol or iso-propanol and in their mixtures with water, at any ratio Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64 from BASF AG.

Natural non-ionic polymers are as well suitable for the composition of the present invention. Those are such as cellulose, chitosan, guar gum, neutralised shellac and their derivatives.

As amphoteric polymers which can be used alone or in mixture with at least one additional cationic and/or nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth) acrylic acid and itaconic acid, with monomers such as mono- or dialkyl aminoalkyl (meth)acrylates or mono- or dialkyl aminoalkyl (meth)acrylamides containing basic groups, in particular amino groups; copolymers from N-octyl acrylamide, methyl methacrylate, hydroxypropyl methacrylate, N-tert.-butyl aminoethyl-methacrylate and acrylic acid, as well as the copolymers known from U.S. Pat. No. 3,927,199.

Anionic polymers may as well be contained in compositions of the present invention. Suitable ones are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/ crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof of the type "Reten®"; etc.

Composition of the present invention may comprise cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643.

Concentration of polymers of anionic, cationic, non-ionic and/or amphoteric or zwitterionic character is in the range of 0.1-15%, preferably 0.5-12.5% and most preferably 1-10% by weight, calculated to the total composition.

The composition of the present invention comprises at least one polyol at a concentration of 5% or more, preferably 7.5% or more and more preferably 10% or more by weight calculated to the total concentration. Maximum concentration of at least one polyol is preferably 30% and more preferably 25% by weight calculated to total composition. The most preferred ones are glycerine, propylene glycols, butylene glycol and hexylene glycol. Further suitable one is sorbitol. It is also the preferred embodiment of the present invention that the compositions comprise at least two different polyols such as glycerine together with propylene or hexylene or butylene glycols.

The anionic polymer of taurate type is the third component of the inventive composition. The polymer is commercially available from Lamberti spa under the trade name Viscolam AT 100/P and is an admixture with hydrogenated polydecene and trideceth-10. Concentration of the taurate type of anionic polymer, poylacryloyldimethyl taurate, is in the range of 0.1 to 10%, preferably 0.5 to 7.5% and more preferably 0.5 to 5% and most preferably 1 to 5% by weight calculated to total composition.

The styling compositions according to the present invention may comprise at least one silicone oil as the fourth essential component. Preferred silicone oils are known with their INCI name as dimethicone, dimethiconol, cyclomethicone and phenyltrimethicone. Commercially, they are available from various companies for example Dow Corning with the known DC series, Wacker Chemie and Toray silicones. All commercially available non volatile silicones are suitable in the compositions of the present invention. Examples to those are DC 200 series, DC1401, DC 1403, DC 1501 and DC 1503. Concentration of silicone oils in the compositions of the present invention is typically between 1 to 20% by weight calculated to total composition. Volatile silicone oils can as well be contained in the hair treatment compositions in mixture with nonvolatile silicone oils within the scope of the present invention with the condition that their content should not exceed ¼, preferably ⅟10 of the nonvolatile silicone oil content of the composition.

Cationic silicones know with INCI name as amodimethicone can as well be contained in the compositions of the present invention. Commercially it is available under the trade name DC 949 in emulsified form in mixture with a nonionic surfactant and a cationic surfactant.

Cationic surfactants may as well be incorporated into the styling compositions of the present invention. The cationic surfactants useful in the compositions are according to the general formula below:

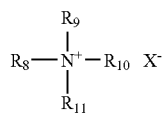

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4. and $R_9$ is a hydrogen, lower alkyl chain with 1 to 4 carbon atoms, saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4. and $R_{10}$ and $R_{11}$ are independent from each other H or lower alkyl chain with 1 to 4 carbon atoms, and X is chloride, bromide or methosulfate.

It should be noted that quaternary ammonium compounds with single alkyl chain are preferred. Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

Concentration of at least one cationic surfactant of the above general formula is in the range of 0.01 to 2%, preferably 0.05 to 1.5% by weight and more preferably 0.1 to 1% by weight calculated to total composition.

Composition of the present invention comprises one or more natural and/or synthethic oil and/or mineral oil at a concentration of 0.1% to 15%, preferably 0.5 to 10% and most preferably 1.5 to 7.5% by weight calculated to total composition, Suitable natural oils are such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention, It should as well be noted that hair treatment compositions can contain mixture of one or more natural oils and mineral oil.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

The compositions according to the invention may also comprise further agents, such as protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis". 4$^{th}$ Ed.

The hair treatment compositions compositions may contain one or more organic solvents within the scope of the invention, such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol.

Compositions of the present invention may contain UV filters either for stabilization of the product colour or for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxybenzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher.

The preferred amount of the UV-absorber ranges from about 0.01% to 1% by weight, calculated to the total composition. Attention should be paid to the stability and appearance especially when using UV filter as salts, e.g. anionic UV filter salts.

Compositions of the present invention can be applied onto hair either by spraying or by rubbing into hair with fingers. In the case that the compositions are intended to be applied by spraying, it is the preferred embodiment of the present invention that it comprises organic solvent at a concentration of maximum 65% by weight calculated to total composition. The preferred organic solvent is ethanol. The preferred lowest concentration is 40% by weight calculated to total composition. The compositions thus obtained show viscosity values lower than 1000 mPa·s., preferably lower than 500 mPa·s, typically between 50 and 250 mPa·s. measured at room temperature with a Brookfield viscosimeter with a suitable spindle and rotation speed, for example Spindle 1 at 25 rpm.

The compositions can also be in the form of a thickened gel. These compositions comprise preferably organic solvents at a concentration with a maximum of 45%, preferably 30% and more preferably 20% by weight calculated to total composition. The viscosity of these compositions is above 1,000 mPa·s measured with a Brookfield viscosimeter at 20° C. with a suitable spindle and rotation speed, for example spindle 5 at 10 rpm. Viscosity values are preferably in the range of 5000 to 50000 mPa·s, more preferably 7500 to 40000 mPa·s and most preferably 10000 to 30000 mPa·s.

pH of the compositions vary between 3 to 9, preferably 4 to 8 and more preferably 5 to 8 measured at room temperature.

The following examples are to illustrate the invention and non-limiting.

EXAMPLE 1

|  | % by weight | | |
| --- | --- | --- | --- |
|  | A | B | C |
| VP/VA Copolymer | 5 | 5 | 5 |
| Glycerin | — | 10 | 10 |
| Propylene gylcol | — | 10 | 10 |
| Viscolam AT 100 P | — | — | 2 |
| Ethanol | 50 | 50 | 50 |
| Aminomethylpropanol | q.s. to pH 6.00 | | |
| Water | to 100 | | |

The compositions A and B are not in accordance with the invention and for comparative purposes. The composition C is according to the invention and has a viscosity of 150 mPa·s measured at 20° C. with the above mentioned method.

The above compositions were tested in a laboratory test for their curl retention and curl separation ability. It was found out that the composition C in accordance of the present invention showed the best curl retention and curl separation ability.

In a further test, the compositions A and B were compared to composition C in a half side test with female volunteers having curly hair. For this purpose, the hair of the volunteers was washed with a regular commercially available shampoo and subsequently approximately 3 g of the test compositions were applied onto each side of the hair by spraying from a bottle equipped with a pump spray (the amount given is for per half side). Hair dressers were asked to evaluate curl appearance, curl separation, shine and hair manageability.

In the first test, composition A vs C, in all cases the appearance of the curls (curl retention and curl separation), shine and manageability were found to be much better at the side treated with inventive composition C.

In the second test composition B vs C, the curl appearance (curl retention and curl separation) was found to be in 50% of the cases much better for the side tested with composition C and in the remaining 50% the side treated with composition C was judged to be better than the composition B. Shine was observed to be better in 70% of the cases for the side treated with the inventive composition and manageability was as well judged to be better in 70% of the case with the inventive composition.

From the above results the conclusion is clear that the inventive composition improves curl retention, curl separation and shine and manageability of hair.

Similar results were obtained with the examples below.

EXAMPLE 2

| VP/VA Copolymer | 5 |
| Glycerin | 10 |
| Propylene gylcol | 10 |
| Viscolam AT 100 P | 3 |
| DC 1503 fluid | 2 |
| Cetrimonium chloride | 0.1 |
| Aminomethylpropanol | q.s. to pH 6.8 |
| Fragrance, preservative | q.s |
| Water | to 100 |

Viscosity of the composition was 18000 as measured at 20° C. with the above method.

EXAMPLE 3

Spayable

| VP/VA Copolymer | 10 |
| Glycerin | 5 |
| Propylene gylcol | 10 |
| Viscolam AT 100 P | 2 |
| Ethanol | 55 |
| Isopropylpalmitate | 3 |
| Cetrimonium chloride | 0.1 |
| Aminomethylpropanol | q.s. to pH 6.8 |
| Fragrance, preservative | q.s |
| Water | to 100 |

Viscosity of the composition is 125 mPa·s. measured with the method given above at 20° C.

EXAMPLE 4

| VP/VA Copolymer | 7.5 |
| Glycerin | 10 |
| Propylene gylcol | 5 |
| Viscolam AT 100 P | 2 |
| Oilve oil | 3 |
| Cetrimonium chloride | 0.1 |
| Benzophenone-3 | 0.1 |
| Aminomethylpropanol | q.s. to pH 6.2 |
| Fragrance, preservative | q.s |
| Water | to 100 |

Viscosity of the composition is 25000 mPa·s. measured with the method given above at 20° C.

The invention claimed is:

1. A method for increasing curl retention of hair, the method comprising:
preparing a hair styling composition comprising at least one film forming polymer, at least one polyol at a concentration of more than 5% by weight calculated to total composition and polyacryloyl dimethyl taurate and/or its salts, wherein the at least one film forming polymer is selected from a non-ionic polymer, an anionic polymer and a combination thereof, wherein the hair styling composition further comprises at least one cationic surfactant at a concentration of 0.01 to 2% by weight calculated to total composition; and
increasing curl retention of hair by applying the hair styling composition to the hair, wherein the hair styling composition is applied to the hair by spraying the hair styling composition onto the hair or by rubbing the hair styling composition into the hair.

2. The method according to claim 1, wherein the at least one film forming polymer is present at a concentration of 0.1 to 15% by weight calculated to total composition.

3. The method according to claim 1, wherein the polyacryloyl dimethyl taurate and/or its salts is present at a concentration of 0.1 to 10% by weight calculated to total composition.

4. The method according to claim 1, wherein two or more polyols are present at a concentration of 5% or more calculated to total composition.

5. The method according to claim 1, wherein the hair styling composition further comprises at least one silicone oil.

6. The method according to claim 1, wherein the hair styling composition further comprises natural and/or synthetic and/or mineral oil.

7. The method according to claim 6, wherein the hair styling composition further comprises at least one fatty alcohol fatty acid esters as a synthetic oil component.

8. The method according to claim 1, wherein the hair styling composition further comprises at least one UV filter.

9. The method according to claim 1, wherein the hair styling composition further comprises organic solvent at a concentration of maximum 65% by weight calculated to total composition.

10. The method according to claim 1, wherein the hair styling composition has a pH between 3 and 9.

11. The method according to claim 1, wherein the hair was shampooed and towel dried before the application of the hair styling composition to the hair.

12. The method according to claim 1, further comprising: air-drying the hair or drying the hair with an electrical hair drier.

13. A method for increasing curl retention of hair, the method comprising:
preparing a hair styling composition comprising (1) at least one film forming polymer, (2) at least one polyol at a concentration of more then 5% by weight calculated to total composition, (3) poylacryloyl dimethyl taurate and/or its salts and (4) at least one cationic surfactant at a concentration of 0.01 to 2% by weight calculated to total composition, wherein the at least one cationic surfactant comprises one or more quaternary ammonium compounds,
increasing curl retention of hair by applying the hair styling composition to the hair, wherein the hair styling composition is applied to the hair by spraying the hair styling composition onto the hair or by rubbing the hair styling composition into the hair.

14. The method according to claim 13, wherein the hair was shampooed and towel dried before the application of the hair styling composition to the hair.

15. The method according to claim 13, further comprising: air-drying the hair or drying the hair with an electrical hair drier.

16. The method according to claim 1, wherein the hair styling composition is in a form of a thickened gel.

17. The method according to claim 1, wherein the hair styling composition is applied to the hair by spraying the hair styling composition onto the hair from a bottle equipped with a pump spray.

18. The method according to claim 13, wherein the hair styling composition is in a form of a thickened gel.

19. The method according to claim 13, wherein the hair styling composition is applied to the hair by spraying the hair styling composition onto the hair from a bottle equipped with a pump spray.

* * * * *